United States Patent [19]
Pyle

[11] Patent Number: 5,824,913
[45] Date of Patent: Oct. 20, 1998

[54] PORTABLE GYRATORY COMPACTOR AND EXTRUDER WITH A SINGLE PIVOT AND TWO GYRATION ACTUATORS

[75] Inventor: Roger A. Pyle, Clarion, Pa.

[73] Assignee: Pine Instrument Company, Grove City, Pa.

[21] Appl. No.: 781,658

[22] Filed: Jan. 10, 1997

[51] Int. Cl.$^6$ ....................................................... G01N 3/08
[52] U.S. Cl. ................................................. 73/818; 73/824
[58] Field of Search ............................ 73/824, 825, 822, 73/820, 843, 85, 818, 865.3, 866

[56] References Cited

U.S. PATENT DOCUMENTS

| | | | |
|---|---|---|---|
| 2,972,249 | 2/1961 | McRae et al. | 73/824 |
| 3,461,717 | 8/1969 | Dunlap et al. | 73/84 |
| 4,942,768 | 7/1990 | McRae | 73/795 |
| 5,036,709 | 8/1991 | McRae | 73/841 |
| 5,323,655 | 6/1994 | Eagan et al. | 73/84 |
| 5,456,118 | 10/1995 | Hines et al. | 73/843 |
| 5,606,133 | 2/1997 | Hines et al. | 73/824 |

Primary Examiner—George M. Dombroske
Assistant Examiner—Max H. Noori
Attorney, Agent, or Firm—Calfee, Halter & Griswold LLP

[57] ABSTRACT

A portable combined gyratory compactor and extruder for compacting a specimen of material in a mold held in a mold gyration assembly and gyrated about a longitudinal axis as a compaction ram is driven into the mold, and for extruding compacted material from the mold without removing the mold from the mold gyration assembly. The mold gyration assembly is suspended from a spherical bearing pivot positioned lateral to the longitudinal axes of the mold and the compaction ram. The compaction ram is drivingly insertable up into the mold through the bottom of the mold to compact material in the mold as the mold is gyrated by the mold gyration assembly. When the gyratory compaction is completed, a top cap assembly over the top of the mold is removed to allow the compaction ram to be driven farther upward into the mold to extrude compacted material through the open top of the mold while the mold is held in the mold gyration assembly. Load cells in a supporting frame are used to measure compaction extent and linear position sensors are used to measure gyration angles of the mold gyration assembly. The device is mounted on a frame with wheels.

30 Claims, 5 Drawing Sheets

PORTABLE GYRATORY COMPACTOR AND EXTRUDER WITH A SINGLE PIVOT AND TWO GYRATION ACTUATORS

FIELD OF THE INVENTION

The present invention pertains generally to apparatus for material compaction testing and, in particular, to apparatus for compacting material held by a mold as the mold is gyrated.

BACKGROUND OF THE INVENTION

Many different types of material testing machines have been designed which hold a material sample and subject it to various forces in order to analyze the material response characteristics. To dynamically test asphalt paving material in particular, it is known that to gyrate a material sample as it is compacted simulates actual response of the material during road construction and to traffic. See, for example, U.S. Pat. Nos. 2,972,249; 4,942,768; 5,036,709; 5,046,367 and 5,275,056. The machines described therein are rather complex and heavily constructed in order to gyrate the mass of the specimen and to impart a substantial compaction force. Consequently, they are not easily operated or transported. This is a disadvantage to the increasing use of such paving material testing machines by paving contractors at construction sites.

Another operational difficulty of such testing machines is the removal of a compacted material sample from a mold to enable analysis of the material. This requires a substantial amount of force, typically applied by a separate extrusion device such as a hydraulic ram, thus requiring the mold to be moved from the compactor to the extrusion device. The necessity of a separate extrusion device is a further disadvantage to portable use of such testing equipment.

SUMMARY OF THE PRESENT INVENTION

The present invention overcomes these and other disadvantages by providing a compact and portable combined gyratory compactor and extruder which is mountable upon a mobile frame. A compaction ram which compacts material in a mold also functions as an extruder which extrudes or pushes compacted material out of the mold in the same direction in which it is compacted. The mold is gyrated by eccentric crank actuators positioned laterally of the compaction ram so that the compaction ram is free to pass completely through the mold.

In accordance with certain aspects of the invention, a combined gyratory compactor and extruder for compacting a specimen of material in a mold held in a mold gyration assembly and gyrated about a longitudinal axis as a compaction ram is driven into the mold, and for extruding compacted material from the mold without removing the mold from the mold gyration assembly. The mold gyration assembly is suspended from a spherical bearing pivot attached to a supporting frame and gyrated by two mold gyration actuators attached to the frame and to the mold gyration assembly and ram. The compaction ram is drivingly insertable up into the mold through the bottom of the mold to compact material in the mold as the mold is gyrated within the mold gyration assembly by the gyration actuators. When the gyratory compaction is completed, a top cap assembly over the top of the mold is removed to allow the compaction ram to be driven farther upward into the mold to extrude compacted material through the open top of the mold while the mold is held in the mold gyration assembly.

In accordance with other aspects of the invention, a portable gyratory compactor and extruder includes a mobile frame which supports a compaction ram and a ram driving motor, a material mold for receiving a material specimen to be compacted, eccentric crank actuators connected to a mold gyration assembly and linearly driven by respective gyration motors positioned laterally of the compaction ram to gyrate the mold about the compaction ram as the ram is driven upward through the bottom of the mold.

In accordance with still other aspects of the invention, a gyratory compactor and extruder device is described for compacting a material within a mold as the mold is gyrated about an axis of the mold, and for extruding compacted material out of the mold. The device includes a frame which supports a mold gyration assembly and a compaction ram, the mold gyration assembly connected to the frame at a point lateral to a longitudinal axis of the mold gyration assembly; a mold for receiving a material to be compacted, the mold dimensioned to be inserted into and held by the mold gyration assembly; mold assembly gyration actuators connected to the mold gyration assembly and operative to gyrate the mold gyration assembly about a longitudinal axis of the mold; the compaction ram operative to travel upward through a bottom of the mold and into the mold to compact material within the mold as the mold is gyrated within the mold gyration assembly by the mold assembly gyration actuators, and a removable cap assembly attached to the frame over an open top of the frame and mold, whereby the cap assembly can be removed following compaction of material in the mold and the compaction ram driven farther upward into the mold to force compacted material through the open top of the mold and frame.

In accordance with still further aspects of the invention, a gyratory compaction and extrusion device is disclosed for compacting a material specimen within a mold as the mold is gyrated about a longitudinal axis of the mold, the device including means for pivotally supporting a mold whereby the mold can be gyrated about a longitudinal axis of the mold, compaction means positioned to be axially driven upward through an open bottom of the mold against a mold bottom plate which fits within the mold, gyration means for gyrating the means for pivotally supporting a mold, said gyration means comprising eccentrically mounted gyration actuators, and a cap which blocks an open top of the mold whereby material can be compacted within the mold by the compaction means as the mold is gyrated.

In accordance with a further aspect of the invention, a floating ram foot for attachment to a distal end of a ram, the floating ram foot including a ram foot mount attachable to a distal end of a ram, a generally conical fitting attached to a ram foot plate, a spring connected to the ram foot mount and to the generally conical fitting, and a thrust bearing connected to the ram foot plate between the ram foot plate and the ram foot mount, the thrust bearing having an internal diameter greater than an external diameter of the generally conical fitting, whereby the spring biases the generally conical fitting into contact with the thrust bearing and the ram foot plate and generally conical fitting have freedom of movement in a space in the ram foot mount between the generally conical fitting and the thrust bearing.

In accordance with a method of the invention of compacting a specimen of material within a mold with a compaction ram as the mold is gyrated, and extruding compacted material from the mold with the compaction ram, the method steps of charging a mold with a specimen of material to be compacted, securing the mold in a mold gyration assembly, capping an open top of the mold, driving a compaction ram into the mold through an open bottom of the mold, gyrating the mold gyration assembly as the compaction ram is driven into the mold, stopping the compaction ram at a desired extent, uncapping the open top of the mold, and driving the compaction ram farther up into the mold to force compacted material out of the mold through the open top of the mold are described.

These and other aspects of the present invention are herein described in particularized detail with reference to the accompanying Figures.

DETAILED DESCRIPTION OF PREFERRED AND ALTERNATE EMBODIMENTS

Figure 1:
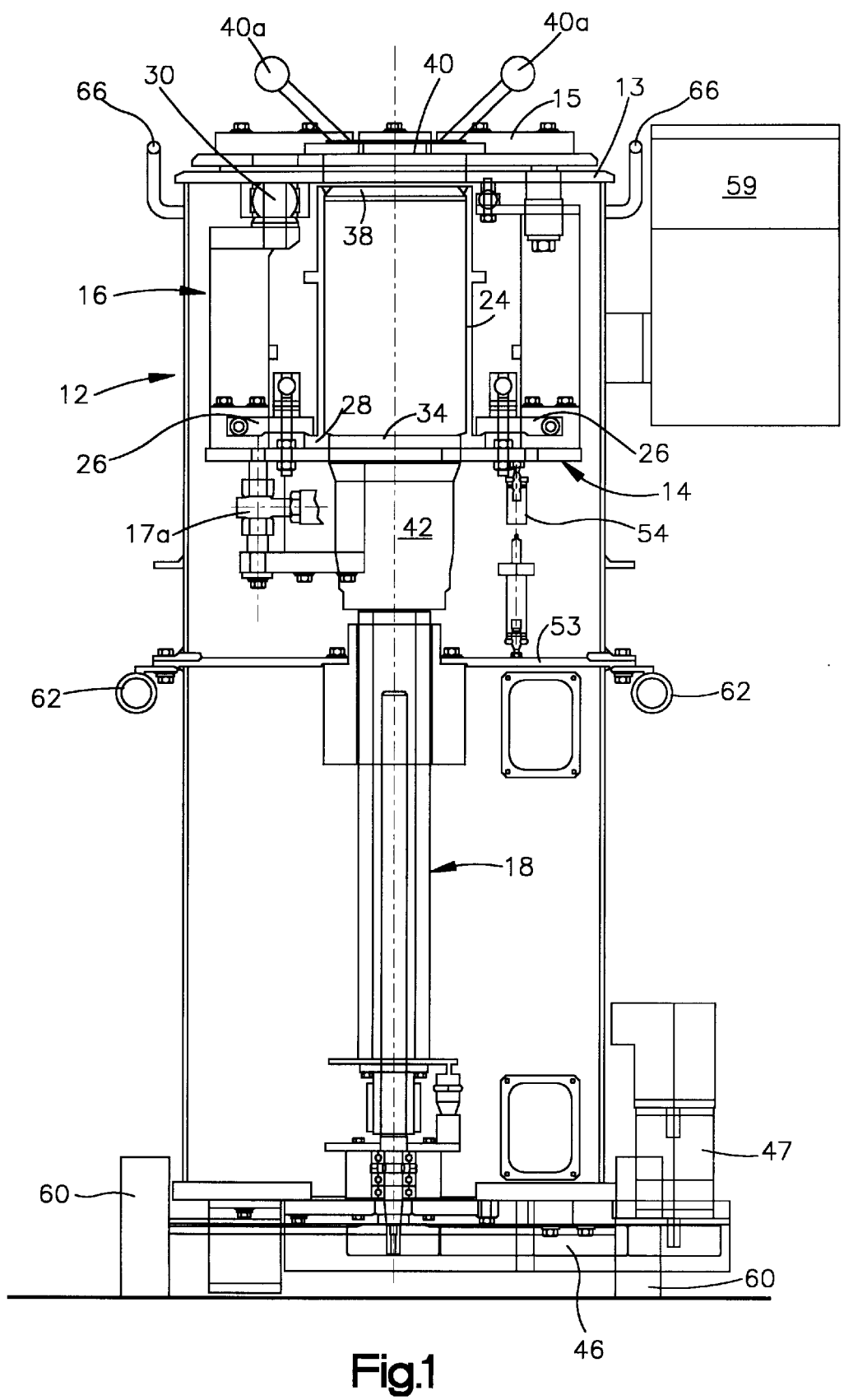
FIG. 1 is an elevation of the combined gyratory compactor and extruder device of the present invention.

With reference to the Figures, there is illustrated a portable combined gyratory compactor and extruder, indicated generally at 10, which includes a generally cylindrical frame 12 which supports a mold gyration assembly 16 (including a mold support table 14) and a compaction ram 18. The frame further supports mold gyration actuators 20a and 20b which are mounted laterally of the mold gyration assembly and compaction ram, and connected to the mold gyration assembly by gyration actuator arms 22a and 22b. A generally cylindrical mold 24 is positionable onto the mold support table 14 and secured to the mold gyration assembly 16 by two or more mold clamps 26 which clamp a peripheral flange 28 of mold 24 to the mold support table 14 to secure the mold to the mold gyration assembly.

Figure 2:
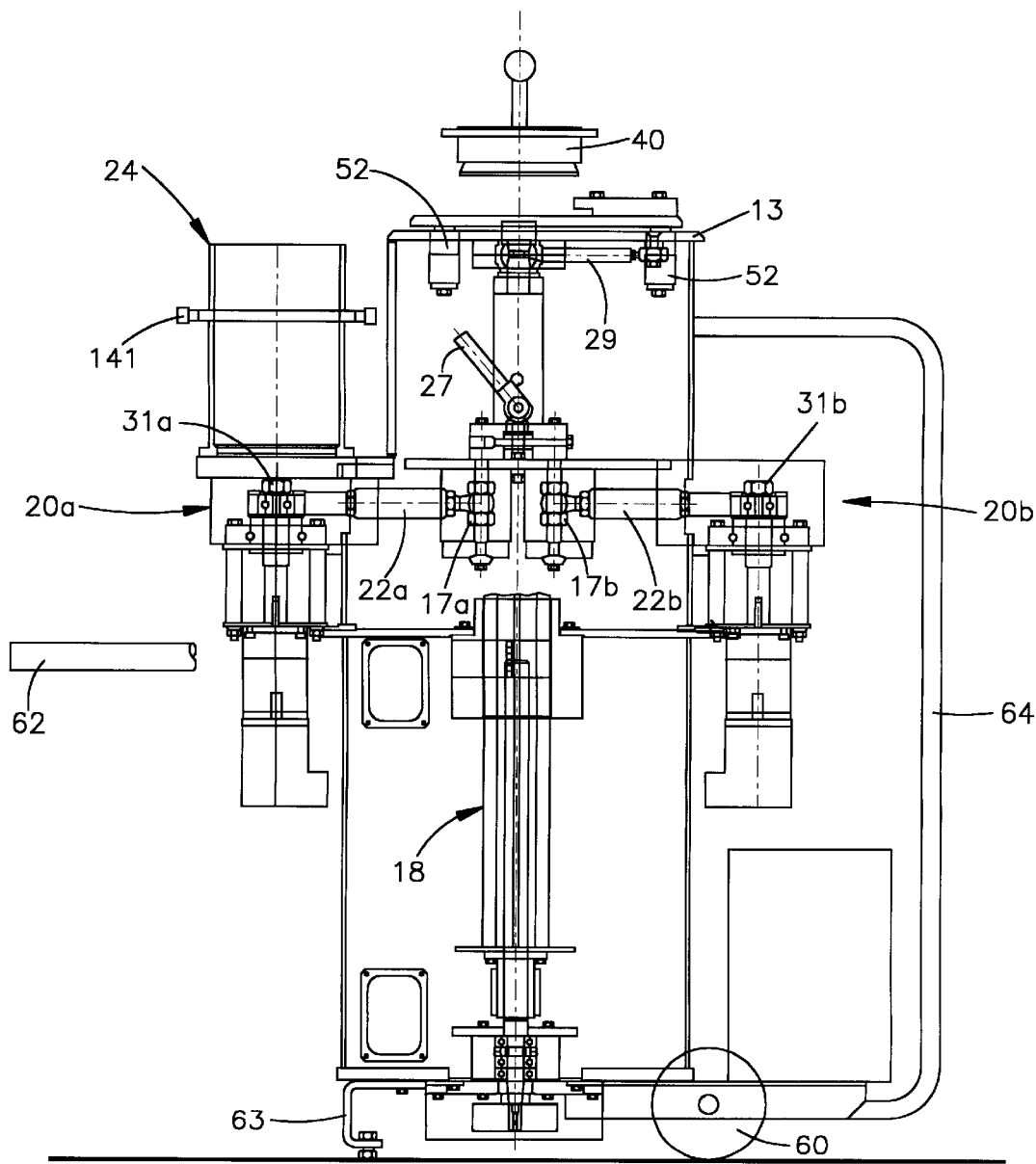
FIG. 2 is an elevation of the combined gyratory compactor and extruder in the direction of arrows 2—2 in FIG. 3.
Figure 3:
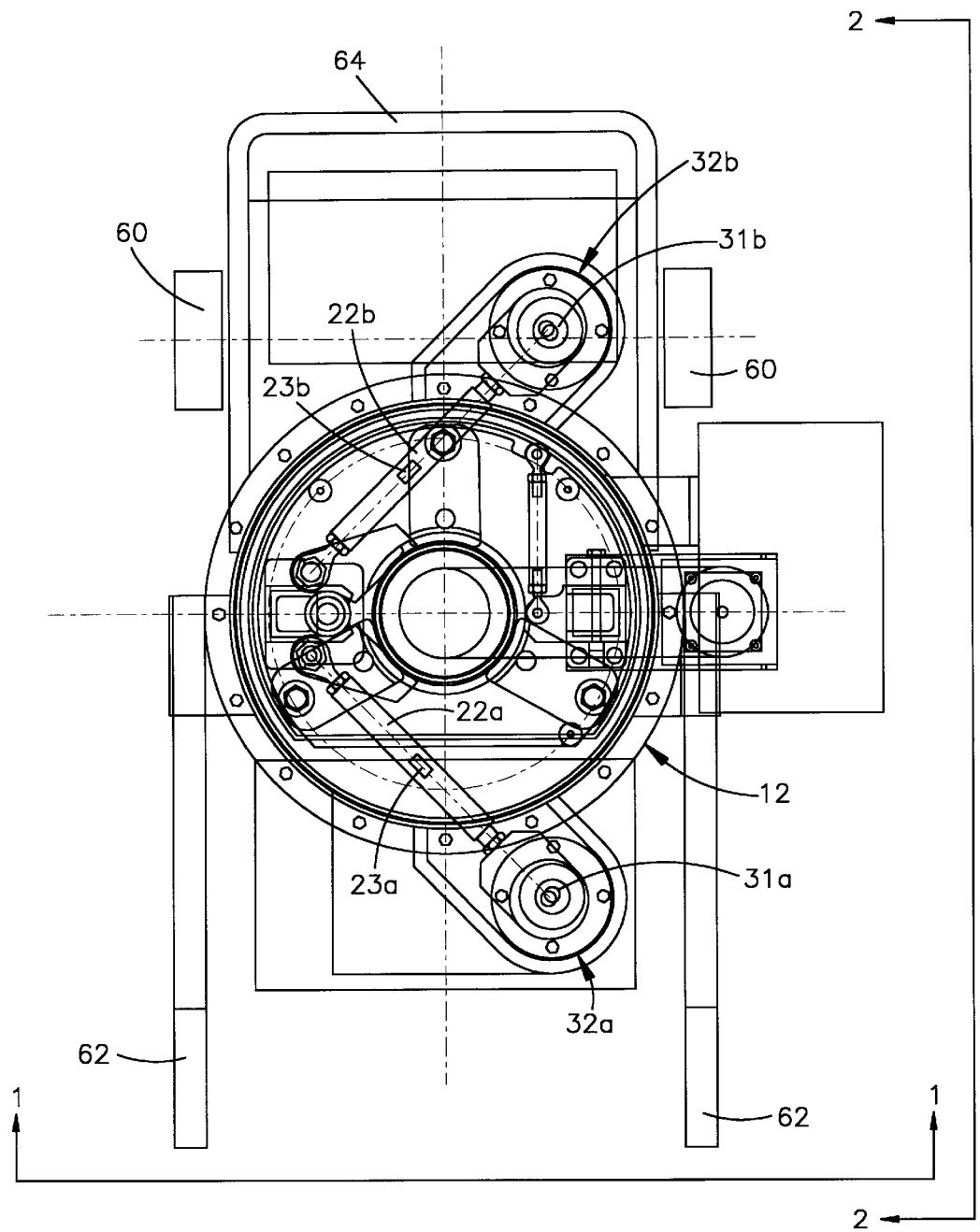
FIG. 3 is a top cross-sectional view of the combined gyratory compactor and extruder of FIG. 1.

The mold gyration assembly is vertically connected to a single spherical bearing-type pivot 30, positioned lateral to the mold and the compaction ram, and connected to a frame top plate 13. In order to prevent rotation of the mold gyration assembly 16 within the frame, a horizontal anti-rotation link 29 extends from pivot 30 to a point lateral to pivot 30 and fixed to frame top plate 13. As shown in FIGS. 2 and 3, the gyration actuator arms 22a and 22b are eccentrically mounted to the respective shafts 31a and 31b of mold gyration actuator motors 32a and 32b. With the opposite ends of actuator arms 22a and 22b connected to the mold gyration assembly 16, eccentric driving of the arms in phase imparts gyration to the gyration assembly and a mold clamped thereto at a gyration angle equivalent to the eccentricity of the connection of the actuator arm to the respective drive motor. Alternatively, the gyration actuator arms 22 may be hydraulic or pneumatically operated linear actuators cycled to gyrate the mold gyration assembly. The entire mold gyration assembly 16 and mold 24 are thus free to gyrate about a point on the longitudinal axis of the mold (and compaction ram) at the points of connection of the gyration acutator arms to the mold gyration assembly. "Gyration" refers to the motion of a point along the longitudinal axis of the mold tracing a circular path concentric with a longitudinal axis of the compaction ram, while another segment or point of the mold axis intersects the axis of the compaction ram. The degree of gyration may be adjusted by an adjustable vertical links 17a and 17b at the respective points of attachment of the actuator arms 22a and 22b to the mold gyration assembly, and/or by the eccentric or linear extent of travel of the gyration actuators.

The mold gyration actuator motors 32a and 32b are preferably electric stepping motors with separate but integrated speed controls, but may alternatively be dc motors with brakes, servo motors, ac synchronous motors, hydraulic or pneumatic. To obtain larger variations in the gyration angle of the mold gyration assembly (and a mold held therein) than link 17 permits, various eccentricities may be used at the points of connection of the gyration actuator arms 22 to the motors 32. Also, the length of the actuator arms 22 may be adjusted by threaded fittings at either end or along the length of the arms. Separate control of gyration actuator motors 32a and 32b allows the arms to be positioned out of phase to axially align the mold gyration assembly and mold therein with the axis of the compaction ram as further described below in reference to the extrusion operation of the device.

The open ends of the cylindrical mold 24 are covered for the gyratory compaction operation, at the bottom by a mold bottom plate 34 held inside the mold by overlapping annular flanges, and at the top by a mold top plate 38 attached to a compactor cap assembly 40. The compactor cap assembly 40 (with handles 40a) is removably engaged with a cap assembly coupling 15 (bolted to the frame top plate 13) by overlapping tapered surfaces which frictionally engage upon rotation of the cap assembly relative to the cap assembly coupling. As shown in FIG. 1, with the cap assembly fully engaged upon the frame, the mold top plate 38 is partially inserted into the open top of the mold. The peripheral edges of the mold top plate 38 are tapered to reduce contact with the interior side walls of the mold as it is gyrated.

Figure 4:
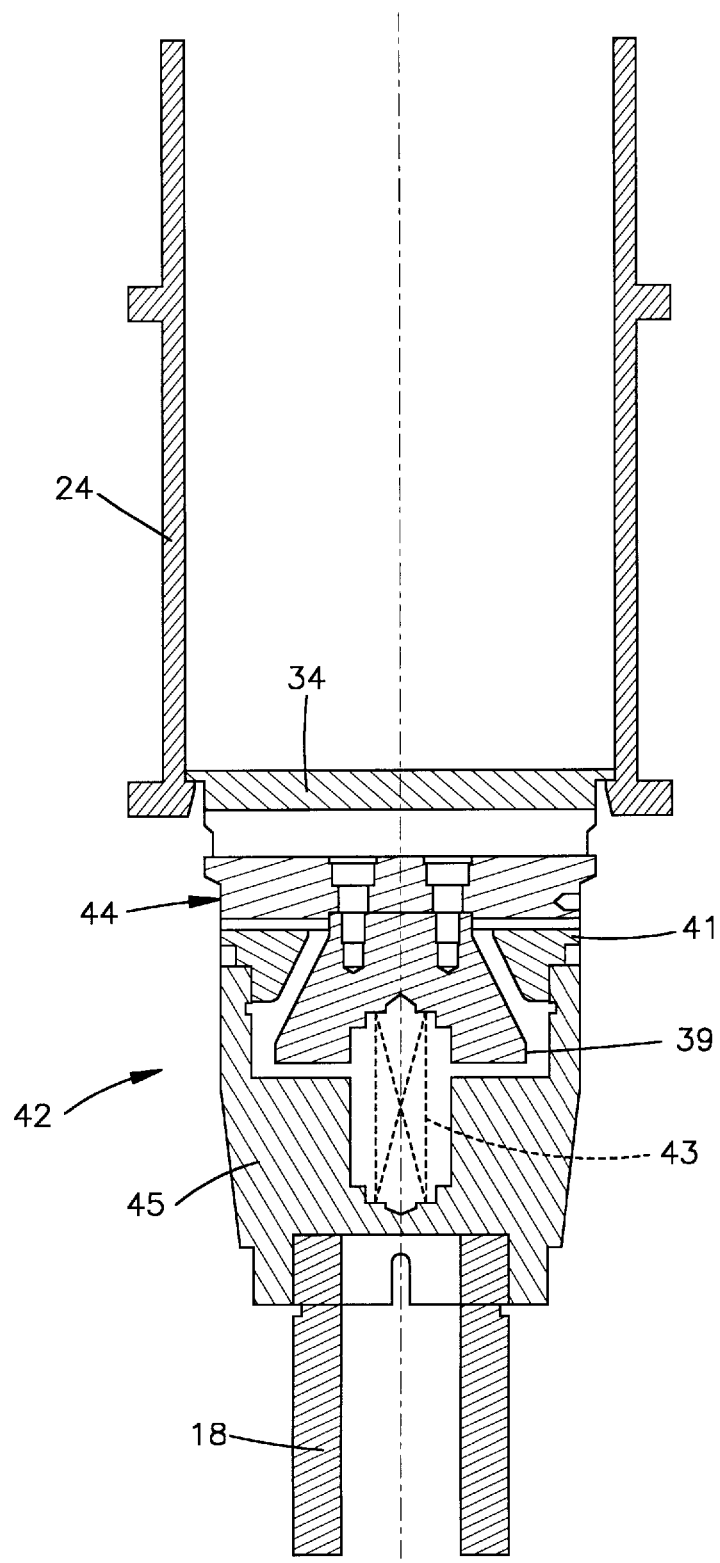
FIG. 4 is a cross-sectional view of the floating compaction ram foot of the present invention.

The compaction ram 18 is attached at an upper distal end to a ram foot 42 which contacts the mold bottom plate 34 upon compaction. As shown in FIG. 4, the ram foot can be made to float in order to follow the gyratory motion of the mold bottom plate by use of a spring mounted floating ram foot plate 44 attached by a spring 43 to a floating ram foot mount 45 which is attached to the upper distal end of the compaction ram 18. A generally conical fitting 39 having an external conical surface is attached to the underside of the floating ram foot plate 44 and fits within a cavity in mount 45. A thrust bearing 41 which has an internal conical surface is also attached to the underside of the ram foot plate 44. The external conical surface of fitting 39 contacts the internal conical surface of retainer thrust bearing 41 when the ram foot plate 44 is unloaded. When the ram foot is loaded, i.e., forced against the mold bottom plate, spring 43 is compressed and the thrust bearing 41 transfers the load from the floating ram foot mount 45 to the ram foot plate 44. The annular spacing between the internal conical surface of the thrust bearing 41 and the external conical surface of the conical fitting 39 allows the ram foot to slide or float with the gyratory motion of the mold bottom plate as the mold is gyrated, and as the compaction ram is advanced upward into the mold. When the ram is retracted, the ram foot plate 44 is unloaded, allowing the spring 43 to extend, but with the thrust bearing 41 reamining within the cavity of mount 45 to maintain axially centering of the ram foot plate 44 so that the ram can be retracted from the mold and is accurately positioned to re-enter the mold in a subsequent operation.

Figure 5:
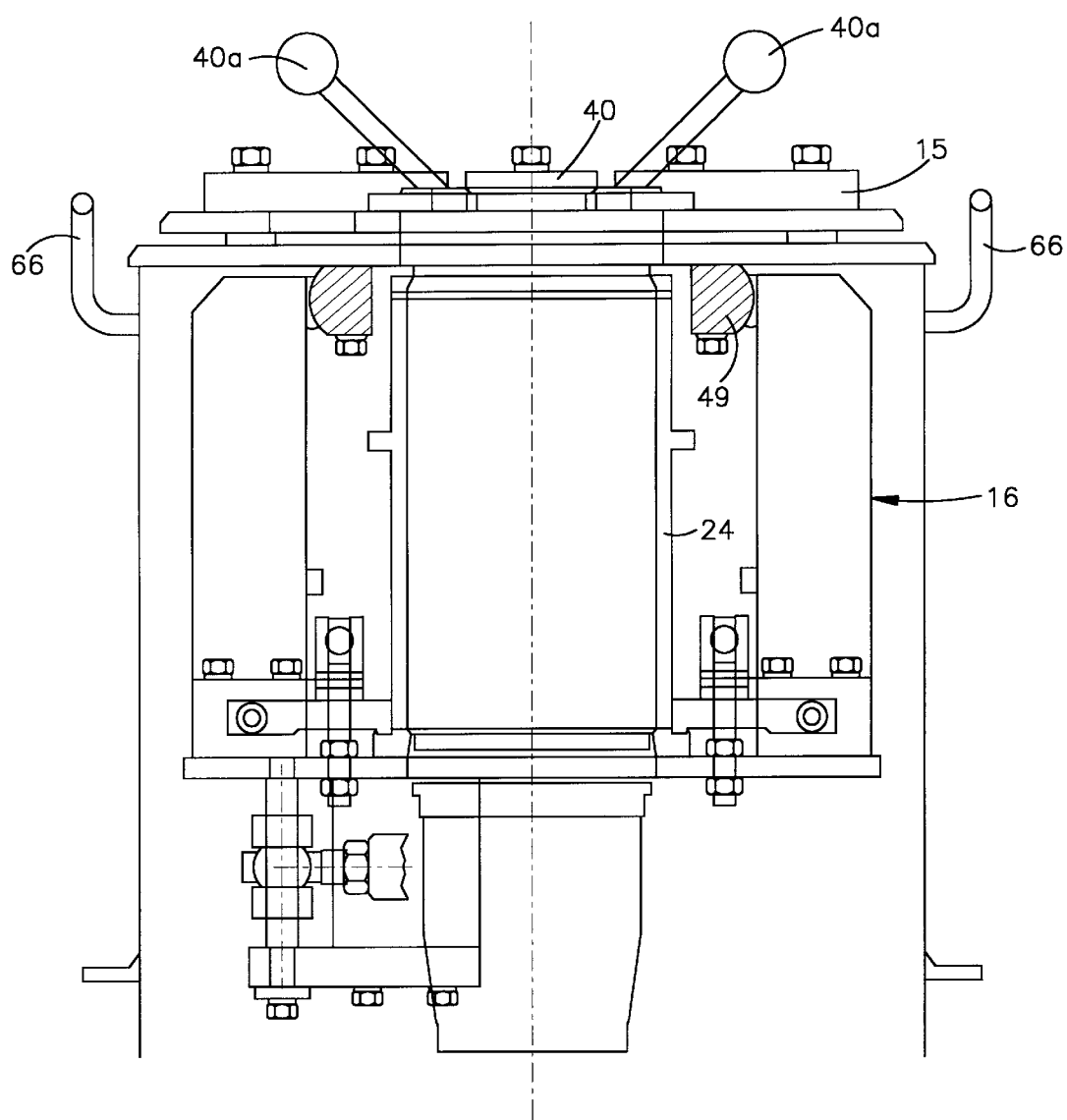
FIG. 5 is a partial elevation of an alternate embodiment of the gyratory compactor and extruder of the present invention.

The gyratory compactor and extruder of the invention may be alternately constructed to position the gyration pivot point on the longitudinal axis of the mold within the mold gyration assembly. For example, with reference to FIG. 5, an annular pivot bearing 49 is attached to frame top plate 13 concentric with the longitudinal axis of the compaction ram and mold 14 within the centered mold gyration assembly. The mold gyration assembly 16 is journalled to follow the outer curved bearing surface of the annular pivot bearing 49, whereby the mold gyration assembly is free to gyrate by the gyration actuators about the bearing.

In operation, a specimen of material to be compacted is inserted in the mold 24 through the open top. The charged mold is placed upon mold support table 14, axially centered within the mold gyration assembly 16 and compaction ram 18, and clamped to the mold gyration assembly by mold clamps 26, manually engaged by a mold clamp operation handles 27. The mold is provided with an annular gripping handle 141. The mold may alternatively be charged when it is positioned within the mold gyration assembly. The compactor cap assembly 40 is then engaged with the cap assembly coupling 15 and the mold top plate 38 thereby positioned within the open top of the mold. With the mold thus positioned and secured, the compaction ram 18 is driven linearly upward against the mold bottom plate 34 and into the mold. The compaction ram may be driven by a screw or ball screw mechanism or hydraulically or pneumatically. A screw jack version of the compaction ram 18 is shown in FIG. 1 rotationally driven by a belt 46 and motor 47. As the ram is driven upward into the mold, the mold is gyrated within the mold gyration assembly about the longitudinal axis of the ram by operation of gyration motors 32a and 32b. In other words, as one gyration actuator arm is eccentrically rotated in phase with the other eccentrically rotated gyration actuator arm, the mold gyration assembly is gyrated about pivot 30, and the mold gyrated about its longitudinal axis coaxial with the longitudinal axis of the compaction ram. As mentioned, similar gyration can be effected by linear gyration actuators.

Once the gyratory compaction process is completed, i.e., the specimen is compacted to a selected degree, the longitudinal axis of the mold is realigned with the longitudinal axis of the ram by centering the mold gyration assembly by separate control of the gyration actuator arms to an out-of-phase or "parked" position. The compaction ram can be controlled (automatically or manually) to back off slightly from the maximum compaction point to relieve pressure from the mold end plates. The cap assembly 40 is removed and the mold top plate along with it. The compaction ram is then driven further upward into the mold to extrude the compacted material out the top of mold while it is still held within the mold gyration assembly. A compacted specimen of material, supported by the mold bottom plate and ram, emerges above the frame top plate 13 whereupon it can be handled directly for further testing and analysis. Thus the need for a separate extrusion device is entirely eliminated by the design of the present invention wherein the axial path of the compaction ram through the mold and the mold gyration assembly is completely unobstructed. Therefore the mold does not have to be removed from the machine or even touched throughout the entire compaction/extrusion process, or between sequential compaction/extrusion processes. For such sequential operation of the device without removing the mold, a mold heater may be placed in contact with the mold within the mold gyration assembly.

Load cells 52 are disposed between the frame top plate 13 and cap assembly coupling 15 and electrically connected to the control system to control the amount of force applied by the ram. A ram position encoder is used to enable calibrated measurements of compaction forces which account for frame deflection. In order to enable measurement and recording of data on gyration angles of the mold gyration assembly during operation of the machine, linear position sensors 54 are located between the mold support table 14 and an internal horizontal shelf member 53 of frame 12 whereby relative movement between the gyration assembly and the frame can be detected and recorded as dynamic gyration angles in a gyratory compaction operation. Also, strain gauges 23a and 23b can be incorporated in respective actuator arms 22a and 22b in order to measure the forces required to gyrate the mold.

A control unit 59 for controlling the compaction ram and gyration actuator motors can also be mounted upon the frame lateral to the upper section for best access by an operator. The control unit 59 may be programmed to, for example, allow single pushbutton start-up of a programmed compaction cycle which starts and stops the compaction ram motor and the gyration actuator motors, and records compaction data from the load cells and gyration data from the linear sensors.

Transport wheels 60 and handles 62 may be attached to the frame 12 to facilitate transport of the entire apparatus in the manner of a balanced two wheel cart or dolly. Feet 63 hold the device in the vertical operation position shown in FIG. 2. Roll bars 64, also attached to frame 12, enable the entire machine to be positioned horizontally upon the major length of the roll bars which provide a stable support for the machine for transport. Righting handles 66 are attached to an upper area of frame 12 to facilitate lifting of the device from the horizontal position to the vertical position.

A combined gyratory compactor and extruder is thus provided which can be easily transported for on-site testing of material such as asphalt. The need for a separate mold extrusion or extraction device is entirely eliminated. Although the invention has been described with specific reference to certain preferred and alternate embodiments, it will be appreciated to those of ordinary skill in the art that certain insubstantial modifications and variations could be made to the device without departing from the scope of equivalents to the invention. For example, such modifications or variations may include location of the gyration pivot at points other than lateral to the mold gyration assembly; orientation of the gyration actuators at points other than lateral to the mold gyration assembly, and different means for adjusting or changing the gyration angles of the mold gyration assembly. All such variations are within the scope of the present invention as defined by the accompanying claims.

The invention claimed is:

1. A combined gyratory compactor and extruder for compacting a specimen of material within a mold as the mold is gyrated and extruding a compacted specimen of material from the mold, the combined gyratory compactor and extruder comprising:

a frame, a mold gyration assembly attached to the frame, the mold gyration assembly having a mold base for supporting a mold, eccentrically driven gyration actuators attached to the frame and to the mold gyration assembly, a mold configured to be positioned within the mold gyration assembly, and a compaction ram axially aligned with the mold gyration assembly and driven to travel up into the mold gyration assembly and into a mold in the mold gyration assembly, the mold having a removable cap assembly attachable over an open top of the mold, whereby the compaction ram travels toward the cap assembly when driven into the mold to compact material between an end of the ram and the cap assembly, and whereby the ram is operative to extrude material through the open top of the mold with cap assembly removed.

2. The combined gyratory compactor and extruder of claim 1 wherein the mold gyration assembly is attached to the frame by a spherical pivot positioned lateral to a longitudinal axis of the compaction ram and mold gyration assembly.

3. The combined gyratory compactor and extruder of claim 1 wherein the eccentrically driven gyration actuators comprise gyration actuator arms eccentrically each connected at one end to a respective gyration actuator motor and at an opposite end to the mold gyration assembly.

4. The combined gyratory compactor and extruder of claim 1 wherein the mold comprises a moveable mold bottom plate contacted by the compaction ram and movable through the interior of the mold.

5. The combined gyratory compactor and extruder of claim 1 further comprising a cap assembly attachable to the frame at a point over the top of a mold in the mold gyration assembly, and a mold top plate attached to the cap assembly and insertable into an open top of the mold when the cap assembly is attached to the frame.

6. The combined gyratory compactor and extruder of claim 1 further comprising clamping means for securing a mold to the mold gyration assembly.

7. The combined gyratory compactor and extruder of claim 2 further comprising a anti-rotation linkage between the mold gyration assembly and the frame.

8. The combined gyratory compactor and extruder of claim 5 further comprising a load cell between the frame and the cap assembly coupling.

9. The combined gyratory compactor and extruder of claim 1 further comprising a linear position sensor between the mold gyration assembly and the frame.

10. A gyratory compactor and extruder device for compacting a material within a mold as the mold is gyrated about an axis of the mold, and for extruding compacted material out of the mold, the device comprising:

a frame which supports a mold gyration assembly and a compaction ram, the mold gyration assembly connected to the frame at a point lateral to a longitudinal axis of the mold;

a mold for receiving a material to be compacted, the mold dimensioned to be inserted into and held by the mold gyration assembly;

mold assembly gyration actuators connected to the mold gyration assembly and operative to gyrate the mold gyration assembly about a longitudinal axis of the mold;

the compaction ram operative to travel upward through a bottom of the mold and into the mold to compact material within the mold against a cap assembly secured over the open top of the mold as the mold is gyrated within the mold gyration assembly by the mold assembly gyration actuators, whereby the cap assembly can be removed following compaction of material in the mold and the compaction ram driven farther upward into the mold to force compacted material through the open top of the mold and frame.

11. The gyratory compactor and extruder device of claim 10 wherin the frame is generally cylindrical.

12. The gyratory compactor and extruder device of claim 10 wherein the mold gyration assembly is connected to the frame by a spherical bearing pivot.

13. The gyratory compactor and extruder device of claim 10 wherein the mold gyration assembly further comprises a mold platform on which a mold is placed, and mold clamps for holding a mold in place on the mold platform in the mold gyration assembly.

14. The gyratory compactor and extruder device of claim 10 wherein the mold is generally cylindrical with an open top and an open bottom.

15. The gyratory compactor and extruder device of claim 14 wherein the mold further comprises a removable mold top plate which covers the open top of the mold and a mold bottom plate which covers the open bottom of the mold.

16. The gyratory compactor and extruder device of claim 15 wherein the mold top plate is attached to the removable cap assembly.

17. The gyratory compactor and extruder device of claim 15 wherein the mold bottom plate is held within the mold by overlapping flanges on the mold bottom plate and on the interior of the mold near the bottom of the mold, whereby the mold bottom plate can move through the interior of the mold in a position perpendicular to a longitudinal axis of the mold.

18. The gyratory compactor and extruder device of claim 15 wherein the compaction ram further comprises a ram foot which contacts the mold bottom plate to push the mold bottom plate through the interior of the mold.

19. The gyratory compactor and extruder device of claim 18 wherein the compaction ram foot comprises a floating ram foot connected by a spring to a ram foot mount.

20. The gyratory compactor and extruder device of claim 10 wherein the mold gyration assembly actuators comprise an actuator arm connected at one end to the mold gyration assembly and connected eccentrically at another end to a rotatable shaft of an actuator motor, whereby driving of the actuator motors in phase causes gyration of the mold gyration assembly in a plane in which the actuator arms are connected to the mold gyration assembly.

21. The gyratory compactor and extruder of claim 10 further comprising load cells in the frame which measure force applied by the compaction ram.

22. The gyratory compactor and extruder of claim 10 further comprising linear position sensors between the mold gyration assembly and the frame operative to measure angles of gyration of the mold gyration assembly relative to the frame.

23. The gyratory compactor and extruder device of claim 10 further comprising a floating ram foot.

24. The gyratory compactor and extruder device of claim 10 further comprising gripping handles and wheels attached to the frame.

25. A gyratory compaction and extrusion device for compacting a material specimen within a mold as the mold is gyrated about a longitudinal axis of the mold, the device comprising:

means for pivotally supporting a mold whereby the mold can be gyrated about a longitudinal axis of the mold, compaction means positioned to be axially driven upward through an open bottom of the mold against a mold bottom plate which fits within the mold, gyration means for gyrating the means for pivotally supporting a mold, said gyration means comprising eccentrically mounted gyration actuators, and a cap which blocks an open top of the mold whereby material can be compacted within the mold by the compaction means as the mold is gyrated.

26. A method of compacting a specimen of material within a mold with a compaction ram as the mold is gyrated, and extruding compacted material from the mold with the compaction ram, the method comprising the steps of:

charging a mold with a specimen of material to be compacted, securing the mold in a mold gyration assembly, capping an open top of the mold, driving a compaction ram into the mold through an open bottom of the mold, gyrating the mold gyration assembly as the compaction ram is driven into the mold, stopping the compaction ram at a desired extent, uncapping the open top of the mold, and driving the compaction ram farther up into the mold to force compacted material out of the mold through the open top of the mold.

27. The method of claim 26 further comprising the step of measuring a force required to gyrate the mold gyration assembly.

28. A portable gyratory compactor device for compacting a specimen of material in a mold as the mold is gyrated, the device comprising a frame for supporting:

a mold for receiving a specimen of material, a compaction means for compacting material within the mold and extruding material from the mold, gyration means for gyrating the mold as the compaction means compacts material within the mold, handle gripping means attached to the frame, rolling means attached to the frame, and roll bars attached to the frame which support the device in a position wherein the rolling means do not contact an underlying surface.

29. The device of claim 25 further comprising a sensor operatively connected to the gyration means.

30. The gyratory compactor and extruder of claim 1 further comprising a strain gauge operatively connected to at least one gyration actuator to measure a force applied to the mold.

* * * * *